(12) United States Patent
Truttmann et al.

(10) Patent No.: US 6,305,260 B1
(45) Date of Patent: Oct. 23, 2001

(54) NON-SYMMETRICAL HEAVY DUTY KNIFE APPARATUS AND CUTTING METHOD

(75) Inventors: Peter Truttmann, Greenville; Jeffrey Allen Plamann, Menasha; John Glen Ahles, Neenah; Robert Lee Holewinski, Menasha, all of WI (US); Brian Dennis Clare, New Milford, CT (US); Timothy Noel Tease, Green Bay, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/416,616

(22) Filed: Oct. 12, 1999

Related U.S. Application Data

(63) Continuation-in-part of application No. 09/020,134, filed on Feb. 6, 1998, now Pat. No. 5,967,009, which is a continuation-in-part of application No. 08/655,506, filed on May 30, 1996, now abandoned.

(51) Int. Cl.$^7$ ...................................................... B26D 3/00
(52) U.S. Cl. ................................ 83/52; 83/346; 83/663; 83/665
(58) Field of Search ............................... 83/52, 346, 663, 83/665

(56) References Cited

U.S. PATENT DOCUMENTS

| | | | |
|---|---|---|---|
| 576,023 | 1/1897 | Bosworth | 83/691 |
| 724,609 | 4/1903 | Peters . | |
| 807,420 | 12/1905 | Copland . | |
| 937,331 | 10/1909 | Reed | 83/663 |
| 1,044,931 | 11/1912 | Simmons | 83/669 |
| 1,499,309 | 6/1924 | Ramsey | 83/685 X |
| 1,557,391 | 10/1925 | Abraham | 83/678 |
| 1,567,887 | 12/1925 | Ackerman | 83/691 |
| 1,778,903 | 10/1930 | Levis . | |
| 1,811,571 | 6/1931 | Ackerman | 83/691 X |
| 1,961,896 | 6/1934 | Barrall | 164/28 |
| 2,525,987 | 10/1950 | Williamson | 407/23 |
| 3,119,312 | 1/1964 | Henc | 83/346 X |
| 3,248,987 | 5/1966 | Cardinet et al. | 83/678 X |
| 3,302,490 | 2/1967 | Bishop | 76/107 |
| 3,348,477 | 10/1967 | Taylor, Jr. et al. | 83/663 X |
| 3,383,969 | 5/1968 | Saunders | 83/663 |
| 3,570,355 | 3/1971 | Spengler | 83/663 |
| 3,663,962 | 5/1972 | Burger | 2/402 |
| 3,880,030 | 4/1975 | Rosengren | 83/9 |
| 4,085,639 | 4/1978 | Marconi | 83/685 X |
| 4,670,960 | 6/1987 | Provost | 29/415 |
| 4,862,574 | 9/1989 | Seidy | 29/415 |
| 5,048,589 | 9/1991 | Cook et al. | 162/109 |
| 5,399,412 | 3/1995 | Sudall et al. | 428/153 |
| 5,826,475 | 10/1998 | Mysliwiec | 83/116 |
| 5,967,009 | 10/1999 | Truttmann et al. | 83/52 |

FOREIGN PATENT DOCUMENTS

| | | | |
|---|---|---|---|
| 670153 | 9/1995 | (EP) . | |
| 731015 | 6/1955 | (GB) | 83/346 |

Primary Examiner—M. Rachuba
(74) Attorney, Agent, or Firm—Thomas J. Connelly; Thomas M. Parker; Douglas G. Glantz

(57) ABSTRACT

A novel knife apparatus and method are disclosed for cutting a plurality of articles from a sheet or web of material. The knife can be formed in or secured to the outer surface of a rotary die cutter. The knife includes a first cutting member having a first end, and second and third cutting members joined to the first end of the first cutting member. The second and third cutting members are arranged relative to one another to form an arcuate section which intersects with the first cutting member to form a non-symmetrical configuration having a cutting edge knife thickness in the range of about 0.003 inches to about 0.005 inches. A unique knife profile enables two adjacently arranged articles to be cut simultaneously from a sheet or web of material with zero clearance between at least a portion of the outer peripheries of the two articles.

17 Claims, 6 Drawing Sheets

ND SYMMETRICAL HEAVY DUTY KNIFE
NON-SYMMETRICAL HEAVY DUTY KNIFE APPARATUS AND CUTTING METHOD

This patent application is a continuation-in-part of U.S. patent application Ser. No. 09/020,134 filed Feb. 6, 1998 U.S. Pat. No. 5,967,009 and U.S. patent application Ser. No. 08/655,506 filed May 30, 1996, now abandoned.

BACKGROUND OF THE INVENTION

1. Technical Field

This invention relates to a novel knife apparatus and method for cutting articles from a sheet or web of material. In one aspect, this invention relates to a knife having a unique configuration which can be formed in or secured to the outer surface of a rotary die cutter for cutting a plurality of articles from a sheet or web of material with zero clearance between at least portions of the outer peripheries of two adjacent articles.

2. Background

Many different kinds and types of articles are manufactured today which entail cutting or stamping out a plurality of identically shaped articles from an elongated sheet or web of material. The sheet or web of material can be a single layer or a laminate formed from two or more layers. In producing such articles, trim waste is usually present, and it is beneficial from a cost standpoint to minimize such waste. Trim waste is defined as all material which does not make up a finished article. It includes waste located adjacent to the periphery of each article as well as waste cut out from the interior of an article. Even when the trim waste is kept to a minimum, its presence still can cause problems in that it has to be separated and conveyed away from the finished articles. The trim waste also must be handled if it is to be properly disposed of, reclaimed, or recycled.

INTRODUCTION TO THE INVENTION

For uniquely configured articles having at least one non-linear edge, it is very difficult to do away completely with trim waste. However, it is possible to minimize the amount of trim waste and to design the waste to have a certain profile so that it can be easier to handle as it is separated from the finished articles.

One way to minimize trim waste is to design the cutting knife to have a profile such that the knife will simultaneously cut two adjacent articles from a sheet or web of material. By arranging two or more articles across and/or along a sheet or web of material such that two articles are joined by a common peripheral segment, a reduction in waste can be obtained.

Now, a novel knife has been invented having a unique configuration formed in or secured to the outer surface of a rotary die cutter for cutting a plurality of articles from a sheet or web of material with zero clearance between at least a portion of the outer peripheries of two adjacent articles.

It is an object of the present invention to provide a knife and method for cutting articles from a sheet or web of material.

A specific object of the present invention is to provide a knife having a unique configuration which can be formed in or secured to the outer surface of a rotary die cutter for cutting a plurality of articles from a sheet or web of material with zero clearance between at least a portion of the outer peripheries of two adjacent articles.

Another object of the present invention is to provide a knife which has a bifurcated configuration which can simultaneously cut a portion of the outer peripheries of two adjacent articles.

A further object of the present invention is to provide a knife which has at least three cutting members intersecting at a common location.

Still another object of the present invention is to provide a knife which will present a more economical way of cutting a plurality of articles from a sheet or web of material.

Still further, an object of the present invention is to provide a die knife having a thickness of at least about 0.003 inches (about 0.075 mm).

These and other objects and advantages of the present invention will become more apparent in view of the following description and the accompanying drawings.

SUMMARY OF THE INVENTION

Briefly, this invention relates to a knife formed in or secured to the outer surface of a rotary die cutter for cutting a plurality of articles from a sheet or web of material. The knife includes a first cutting member having a first end, and second and third cutting members joined to the first end of the first cutting member. The second and third cutting members are arranged relative to one another to form an arcuate section which cooperates with the first cutting member to form a non-symmetrical configuration. The knife and method of the present invention provide a specified cutting edge knife thickness and specified knife configuration for a rotary die cutter in cooperation with a specified proximity to a corresponding rotary anvil. The unique configuration enables two articles to be cut simultaneously from a sheet or web of material with zero clearance between at least a portion of the outer peripheries of the two adjacent articles.

DETAILED DESCRIPTION

Figure 1:
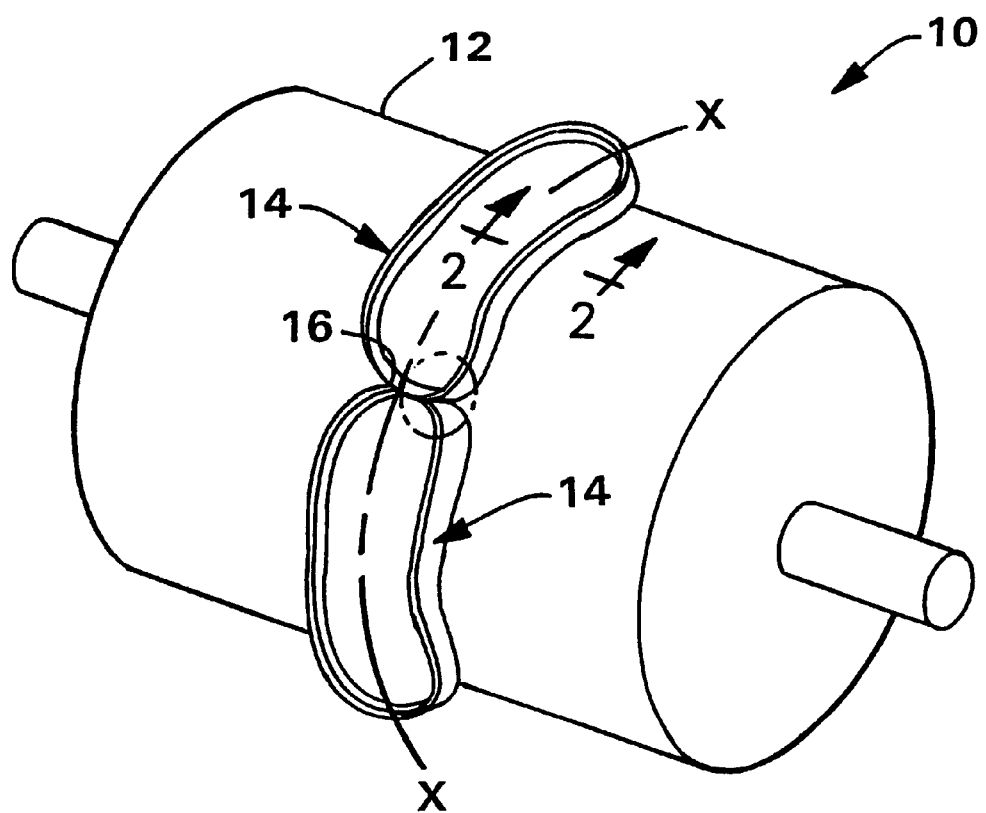
FIG. 1 is a perspective view of a rotary die cutter showing a pair of knives each having an hourglass profile and arranged end to end such that a common section of the knife can simultaneously cut a portion of the outer peripheries of two adjacent articles.

The novel knife of the present invention operates to provide a specified cutting edge knife thickness and specified knife configuration for a rotary die cutter in cooperation with a specified proximity to a corresponding rotary anvil. The specified cutting edge knife thickness and specified knife configuration have been found to provide important advantages of less surface area, less pressure, and more structural integrity to produce longer knife life.

It has been found that the specified cutting edge knife thickness should be in the range of about 0.001 to 0.005 inches. At a cutting edge knife thickness below about 0.001 inches, the knife will cut, but it has been found that the knife will lose the integrity of its cutting member. At a cutting edge knife thickness below about 0.001 inches, it has been found further that the knife is hard to machine into a proper configuration. At a cutting edge knife thickness above about 0.005 inches, the knife will cut, but it has been found that the knife will become prematurely dull and will wear out too quickly. At cutting edge knife thicknesses above about 0.005 inches, the knife surface requires too much pressure, and it wears out very quickly. The excessive pressure flattens out the cutting edge, and even more increased pressure is required to cut.

It has been found that the specified knife configuration should be in the range of about 20% to 70% based on a ratio of the cutting edge surface area to the overall surface area, as described more completely in the detailed description which follows. At a cutting edge knife configuration below about 20% cutting edge surface area to the overall surface area, it has been found that the knife does not have a preferred cross section thickness to supply sufficient structural integrity. At a cutting edge knife configuration below about 20% cutting edge surface area to the overall surface area, it has been found that the knife will cut, but it will have reduced knife life. Longevity of the knife is of key importance in the business of producing sanitary napkin articles from a moving layered sheet of web material in a rotary die cutter. At a cutting edge knife configuration above about 70% cutting edge surface area to the overall surface area, it has been found that the knife bangs against the anvil, even to the point of putting a ding in the anvil. It has been found further that at surface areas above the specified surface area, more pressure is required, and the higher pressure produces a flattening of the knife cutting edge to make it more dull, thereby accelerating an inefficiency problem.

The novel knife of the present invention further operates to provide a specified knife height for a rotary die cutter knife in cooperation with a corresponding rotary anvil. The specified cutting edge knife height has been found to "burst" or "snap" a sanitary napkin article to be cut from a layered sheet, while not cutting all the way through the thickness of the layered sheet. The knife of the present invention operates to cut through only about 80% to 90% of the thickness of the layered sheet. The remainder of the layered sheet, e.g., 10% to 20% of the layered sheet not severed by the cutting edge of the knife, will burst or snap to form the discrete sanitary napkin article. In this manner, the knife of the present invention has been found to get longer life in the cutting edge.

The longevity of the knife is critically important in the business of producing sanitary napkin articles from a moving layered sheet of feed material in a rotary die cutter. The knife of the present invention provides for millions and millions of high speed cuts to produce the sanitary napkin articles from a moving layered sheet. The moving sheet of layered material travels at speeds of 500 feet per minute and higher. The knife life preferably runs to 50 million rotations of the rotary die cutter.

The precision of the knife cutting edge thickness, height, and configuration also has been found to be critically important in producing sanitary napkin articles from a moving layered sheet of feed material in a rotary die cutter. The high speeds of the moving layered sheet and long life of the knife are provided by the novel knife of the present invention. It has been found that the knife of the present invention containing the specified cutting edge thickness, knife height, and knife configuration provides a reduced surface area, less pressure, less wear out, and significantly longer knife life.

The specified knife configuration, in one aspect, preferably provides a specific geometry including a linear section joined to an arcuate section as more particulary described in the detailed description which follows. The specific geometry of the specified knife configuration of the present invention provides for a significantly reduced surface area on the knife cutting area and at the knife junctures. The knife of the present invention reduces surface area at the junction points and significantly reduces pressure points, and significantly increases knife life.

The important key of longer knife life is facilitated dramatically when the knife tip is held away from making actual contact with the anvil. Holding the knife away from the anvil requires an effective cutting precision on the entire knife thickness, height and configuration, or pattern. If the thickness of the cutting edge on the portion of the knife configuration or pattern is not precise, the die must be adjusted downward toward the anvil, thereby producing higher pressure on the knife edge and decreased die life.

The knife of the present invention provides a precision cutting tool, a fine cutting instrument. The knife of the present invention as a precision cutting tool provides significant material savings on the order of in excess of one million dollars per year (1998 dollars) in layered sheet material savings. Further savings are produced by higher rotary die cutter speeds, lower down time of the rotary die cutter manufacturing operation, and reduced knife sharpening expense.

Referring to FIG. 1, a rotary die cutter 10 is shown having an outer periphery 12 which is circular in configuration. Secured to or mounted onto the outer periphery 12 are two or more knives 14 which are depicted having an hourglass configuration and a central longitudinal axis X—X which circumscribes the outer periphery 12 of the rotary die cutter 10. The knives 14 are arranged such that they abut one another and have a common edge 16 located there between. It should be noted that the knives 14 can have any type of configuration desired including a square, a rectangle, a circle, an ellipsoid, an hourglass, or an oval. The knives 14 can be used to cut a sheet of material which includes a single layer or a web of material which includes two or more layers. For the purposes of this detailed description, the knives 14 will be described as being secured to or mounted onto a rotary die cutter, but the knives 14 can be used by themselves or be attached to a movable member or to some other type of rotating or reciprocating mechanism.

For ease of understanding, the present invention will be described in relation to cutting out or stamping out a plurality of absorbent articles such as sanitary napkins, panty liners, or incontinent garments from an elongated sheet or web of material.

Figure 2:
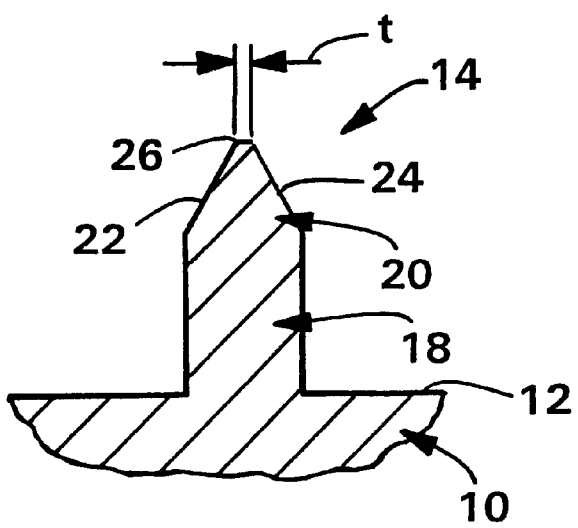
FIG. 2 is a cross-sectional view of one of the knives shown in FIG. 1 taken along line 2—2.

Referring to FIG. 2, the knife 14 is shown integrally formed with the rotary die cutter 10 and extending outward in the radial direction from the outer periphery 12. The knife 14 includes a shank 18 which terminates into a knife blade 20. The knife blade 20 has an inside edge 22 and an outside edge 24, one or both of which may be tapered or inclined toward one another so as to form an apex 26. The apex 26 can be a sharp point or it can be a flat surface as viewed under a microscope. The overall thickness (t) is about 0.0012 inches to about 0.0018 inches (about 0.0305 mm to about 0.0460 mm) when used to cut an absorbent article, such as a panty liner. As the knife blade wears from use, it is possible to regrind one or both of the surfaces 22 and 24 so as to maintain the desired thickness (t) of the apex 26.

As mentioned above, although the knife 14 is shown as integrally attached to the rotary die cutter 10, the knife 14 also can be mounted onto a plate which is then screwed, bolted, or removably attached to the rotary die cutter 10.

Figure 3:
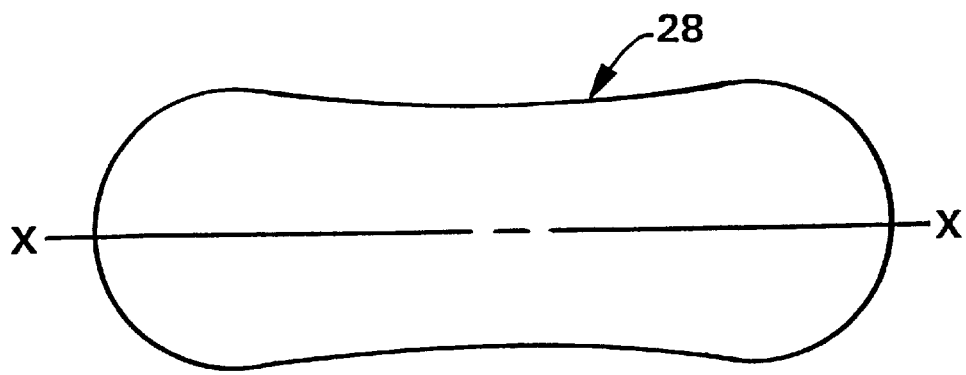
FIG. 3 is a top view of an absorbent article, such as a sanitary napkin or panty liner, and having a central longitudinal axis X—X which has been cut out by the rotary die cutter.
Figure 4:
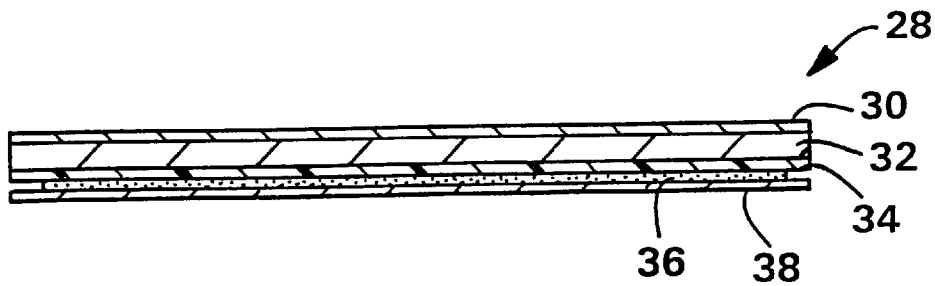
FIG. 4 is a side view of the absorbent article shown in FIG. 3 depicting several distinct layers.

Referring to FIGS. 3 and 4, the knife 14 is designed to cut an article 28 from an elongated sheet or web of material. The sheet or web of material can be a single layer of material, or it can be formed from two or more different, distinct, or identical layers which can be vertically stacked, assembled, laminated, or bonded together. When two or more layers are present, the layers can be laminated or bonded together by heat, pressure, heat and pressure, glue, adhesive, thermal bonds, mechanical bonds, or chemical bonds. The articles 28 can have almost any kind of configuration imaginable. For purposes of illustration, the article 28 is depicted as an elongated panty liner having a central longitudinal axis X—X. However, it should be noted that this invention is not limited to this particular shape. The materials which can be cut by the knife 14 include paper, plastic, film, thermoplastic films, absorbent fluff, coform, foam, wood pulp, cardboard, wood, or any other known material or combination thereof. Coform consists of a spunbonded carrier sheet with a mixture of pulp fibers and extruded polypropylene which is available from Kimberly-Clark Corporation having an office at 401 N. Lake Street, Neenah, Wis. 54956. For purposes of discussion only, the article 28 will be described as an absorbent article such as a sanitary napkin, a panty liner, or an incontinent garment. It should be noted that the knife 14 can cut both linear and nonlinear edges, curves, arcuate shapes, or circles. Articles having a straight or linear segment such as a square, rectangle, or parallelogram profile tend to be easier to nest and die cut in a line-to-line fashion.

As shown in FIG. 1, two knives 14 are formed in a portion of the outer periphery 12 of the solid shaft die cutter 10. The knives 14 are arranged in an end-to-end configuration about the outer periphery 12 of the rotary die cutter 10 and cooperate with other knives 14 (not shown) which would form a row of knives 14 which extend completely around the outer periphery 12. The number of knives 14 which are present will depend on the length of the circumference of the die cutter 10 and the size and shape of the individual knives 14. The knives 14 can be machined into the shaft of the die cutter 10 such that they appear in an offset and/or a side-by-side arrangement. Multiple knives 14 can be machined about the periphery 12 and across the width of the die cutter 10. For example, 2, 3, 4, or 5 knives 14 can be formed about the periphery 12 and across the width of the rotary die cutter 10 so that a plurality of articles can be cut out for each revolution of the die cutter 10. It should be noted that when the knives 14 have an irregular profile, it may be advantageous to nest the knives 14 in a pattern across the width of the die cutter 10, so as to be able to cut out additional articles.

Referring again to FIGS. 3 and 4, the absorbent article 28 is shown which is designed to be attached adhesively to the inner crotch portion of a wearer's undergarment. Such articles nominally consist of several layers of distinct materials which are vertically arranged. The layers, from top to bottom, can include a liquid-pervious cover 30, an absorbent 32, a liquid-impermeable baffle 34, a garment attachment adhesive 36 secured to a lower surface of the baffle 34, and a removable peel strip 38. Other layers, such as a transfer layer, a wicking layer, a layer containing superabsorbent materials, or additional absorbent layers also can be utilized. The various layers can be vertically stacked, assembled, laminated, and/or bonded together to form a multilayer web of material from which the articles 28 then can be cut or stamped out. The various layers can be bonded together by using heat, pressure, heat and pressure, construction adhesive, a hot melt glue, stitching with thread, ultrasonic bonding, mechanical bonding, thermal bonding, chemical bonding, or a combination thereof.

The liquid-permeable cover 30 is designed to contact the body of the wearer and can be constructed of a woven or nonwoven material which is easily penetrated by body fluid. The liquid-permeable cover can be formed from either natural or synthetic fibers. Suitable materials include bonded carded webs of polyester, polypropylene, polyethylene, nylon, or other heat-bondable fibers. Other polyolefins, such as copolymers of polypropylene and polyethylene, linear low-density polyethylene, finely-perforated film webs, and net materials, also work well. A preferred material is a composite of an apertured thermoplastic film positioned above a nonwoven fabric. Such a composite material can be formed by extrusion of a polymer onto a web of spunbond material to form an integral sheet. One example of this is an apertured, thermoplastic polyethylene film bonded to a spunbond material. Spunbond is a nonwoven material which is manufactured and commercially sold by Kimberly-Clark Corporation having an office located at 401 N. Lake Street, Neenah, Wis. 54956. The apertured film/nonwoven laminate exhibits a smooth appearance and is soft to the touch. This material is relatively soft and does not irritate the wearer's skin and yet has a cushioned feel because of its bulk.

Another material useful as the liquid-permeable cover is a spunbond web of polypropylene. This spunbond web can contain from between about 1 percent to about 6 percent of a whitening agent, such as titanium dioxide ($TiO_2$) or calcium carbonate ($CaCO_3$) to give it a clean, white appearance. A uniform thickness of spunbond is desirable because it will have sufficient strength, after being perforated, to resist being torn or pulled apart during use. The most preferred polypropylene webs have a basis weight of between about 18 grams per square meter (gsm) to about 40 gsm. An optimum weight is between about 30 gsm to about 40 gsm.

The absorbent layer 32 can be present as a single layer or as two or more layers. The absorbent 32 can be formed from various natural or synthetic fibers such as wood pulp fibers, virgin cellulose fibers, regenerated cellulose fibers, cotton fibers, peat moss, or a blend of pulp and other fibers. The absorbent layer 32 also could be formed from a fine pore fabric such as wet-laid, air-dried tissue or from an uncreped through-air-dried (UCTAD) tissue having a basis weight of from about gsm to about 120 gsm. The UCTAD tissue can be prepared by a process disclosed in U.S. Pat. No. 5,048, 589 issued to Crook et al. on Sept. 17, 1991. The UCTAD tissue is disclosed in U.S. Pat. No. 5,399,412 issued to Sudall et al. on Mar. 21, 1995. Each of these patents is incorporated by reference and made a part hereof. The absorbent layer 32 also may include other wellknown materials such as cellulose fibers, rayon fibers, cellulose sponge, hydrophilic synthetic sponge, for example polyurethane, and the like.

The liquid-impermeable baffle 34 permits the passage of air or vapor from the absorbent article 28 while blocking the passage of body fluid. The liquid-impermeable baffle 34 is made from material having these properties. The liquid-impermeable baffle 34 also can be constructed from a material that blocks the passage of vapor as well as fluids. A good material from which the baffle 34 can be constructed is a micro-embossed, polymeric film, such as polyethylene or polypropylene. Bicomponent films also can be used. A preferred material is polyethylene film. Most preferably, the baffle 34 is made from a polyethylene film having a thickness in the range of from about 0.5 mm to about 2.0 mm.

It should be noted that construction adhesive can be used in the article 28 to attach and bond the various layers together. For example, construction adhesive can be used to bond the liquid-impermeable baffle 34 to the absorbent 32 or to bond the absorbent 32 to the liquid-permeable cover 30. The presence of such construction adhesive and the amount used will depend upon manufacturing specifications. Useful construction adhesives are sold commercially by National Starch and Chemical Company, having an office located at 10 Findeme Ave., Bridgewater, N.J. 08807.

The absorbent article 28 also can include one or more elongated strips or areas of garment attachment adhesive 36 secured to the bottom surface of the liquid-impermeable baffle 34. The garment attachment adhesive 36 functions to attach the article 28 to the inner crotch portion of the user's undergarment. The garment attachment adhesive 36 enables the absorbent article 28, particularly a sanitary napkin, panty liner, or incontinent garment, to be properly aligned and retained relative to the user's vaginal opening so that maximum fluid protection can be obtained.

The garment attachment adhesive 36 can cover the complete bottom surface of the liquid-impermeable baffle 34 or only a portion of it. The garment attachment adhesive 36 can consist of a swirl pattern of adhesive or be one or more strips of adhesive. The garment attachment adhesive 36 also can consist of a plurality of adhesive dots which are randomly or uniformly arranged on the exterior surface of the baffle 34. When in strip form, the garment attachment adhesive 36 can be aligned along the central longitudinal axis X—X of the absorbent article 28. Alternatively, the garment attachment adhesive 36 can be present as two or more spaced apart longitudinal strips. The garment attachment adhesive 36 is of such a nature that it will allow the user to remove the absorbent article 28 and reposition it on the wearer's undergarment if needed. A hot melt adhesive which works well as the garment attachment adhesive is sold commercially by National Starch and Chemical Company having an office located at 10 Findeme Avenue, Bridgewater, N.J. 08807.

To protect the garment attachment adhesive 36 from contamination prior to use, the adhesive 36 can be protected by a releasable peel strip 38. The peel strip 38 can be a white Kraft paper coated on one side so that it can be released from the adhesive 36. The coating can be a silicone coating, such as a silicone polymer commercially available from Akrosil having an office located 206 Garfield Avenue, Menasha, Wis. 54952. The peel strip 38 is removed by the user prior to attachment of the absorbent article 28 to the inner crotch portion of her undergarment.

Figure 5:
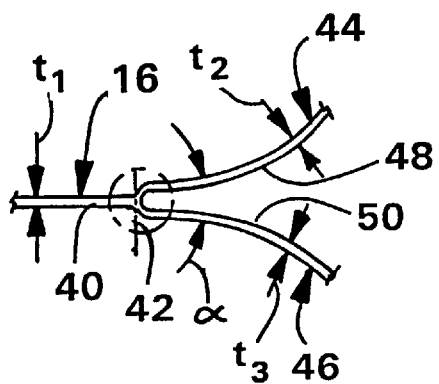
FIG. 5 is an exploded top view of the area within the dotted circled shown in FIG. 1 depicting the bifurcation of the knife.

Referring to FIG. 5, an exploded top view of the knife 14 is shown depicting the common edge 16. The knife 14 includes a first cutting member 40 having a first end 42. The first end 42 is depicted as a dotted line for the purpose of better understanding the invention. The knife 14 also includes a second cutting member 44 joined to the first end 42 of the first cutting member 40. The knife 14 further includes a third cutting member 46 also joined to the first end 42 of the first cutting member 40. It should be noted that by the word "joined," it is meant that the second and third cutting members, 44 and 46 respectively, can be integrally machined or formed from material which forms the first cutting member 40. Additionally, the word "joined" can include the attachment of the second and third cutting members, 44 and 46, respectively, to the first cutting member 40 by means of welding, mechanically bonding, thermally bonding, chemically bonding, or some other type of physical attachment. For best results, the second and third cutting members, 44 and 46, respectively, preferably are machined from a single piece of metal with the first cutting member 40. It should be noted that the entire knife 14 is machined from the solid shaft of the die cutter 10.

The first cutting member 40 can be a linear member formed from ferrous or nonferrous metal. Preferably, the knife 14 is formed from tool steel. The first cutting member 40 should have a thickness t1 of at least about 0.0010 inches+0.0002 inches (0.0254 mm+0.0050 mm), preferably has a thickness of between about 0.0010 inches+0.0002 inches to about 0.0050 inches+0.0002 inches (at least about 0.0254 mm+0.0050 mm to about 0.1270 mm+0.0050 mm), and more preferably has a thickness of between about 0.0010 inches+0.0002 inches to about 0.0030 inches+0.0002 inches (at least about 0.0254 mm+0.0050 mm to about 0.0762 mm+0.0050 mm). The second and third cutting members, 44 and 46, respectively, also can be formed from ferrous or nonferrous metal and preferably are formed from tool steel. The second and third cutting members 44 and 46, respectively, should have a thickness of at least about 0.0010 inches+0.0002 inches (at least about 0.0254 mm+0.0050 mm). Furthermore, the second and third cutting members, 44 and 46, respectively, should have a thickness of between about 0.0010 inches+0.0002 inches to about 0.0050 inches+ 0.0002 inches (about 0.0254 mm+0.0050 mm to about 0.1270 mm+0.0050 mm), preferably a thickness of between about 0.0010 inches+0.0002 inches to about 0.0030 inches+ 0.0002 inches (at least about 0.0254 mm+0.0050 mm to about 0.0762 mm+0.0050 mm). The thickness t2 of the second cutting member 44 and the thickness t3 of the third cutting member 46 can be equal to the thickness t1 of the first cutting member 40. It should be noted that, preferably, the first, second and third cutting members, 40, 44, and 46, respectively, all will have the same thickness within 0.0002 of an inch (0.0050 mm), but may have different thicknesses. For example, the first cutting member 40 can have a thickness t1 which is greater than, equal to, or less than the thickness t2 of the second cutting member 44 and/or of the thickness t3 of the third cutting member 46.

As shown in FIG. 2, the specified knife height above surface 12 should be between about 1/8 inch and about 3/16 inch. At dimensions below about 0.1 inch, the cutting edge is not capable of being machined, and the angle, e.g., 30 degree angle, of the knife leading up to the cutting edge runs into surface 12. Above about 1/4 inch, the structural integrity of the knife is reduced. A moment arm is created by the knife height above surface 12, and a larger moment arm has been found to create cracks in the steel. A larger dimension for the knife height makes for a larger moment arm, and cracks are observed sometimes at the intersection of surface 12 or further down in the steel.

The novel knife of the present invention operates to cut through only about 80% to 90% of the thickness of the layered sheet. The knife is positioned at a specified proximity from the anvil so that the knife operates to cut through only about 80% to 90% of the thickness of the layered web sheet. The remainder of the layered sheet, e.g., 10% to 20% of the layered sheet not severed by the cutting edge of the knife, will burst or snap to form the discrete sanitary napkin article. In this manner, the knife of the present invention has been found to provide significantly longer knife life.

As shown in FIG. 5, the second and third cutting members, 44 and 46, respectively, are arranged relative to one another to form an angle alpha ($\alpha$) there between of 180° or less. Preferably, this angle is between from about 15° to about 180°, more preferably, between from about 30° to about 150° and, most preferably, between from about 45° to about 120°. It should be noted that the angle alpha ($\alpha$) can be measured anywhere between the second and third cutting members, 44 and 46, respectively, and may vary as the configuration of the second and third cutting members 44 and 46 diverge from one another.

The second and third cutting members, 44 and 46, respectively, each has an arcuate section 48 and 50, respectively, which cooperates with the first cutting member 40 to form a general wishbone configuration.

Figure 6:
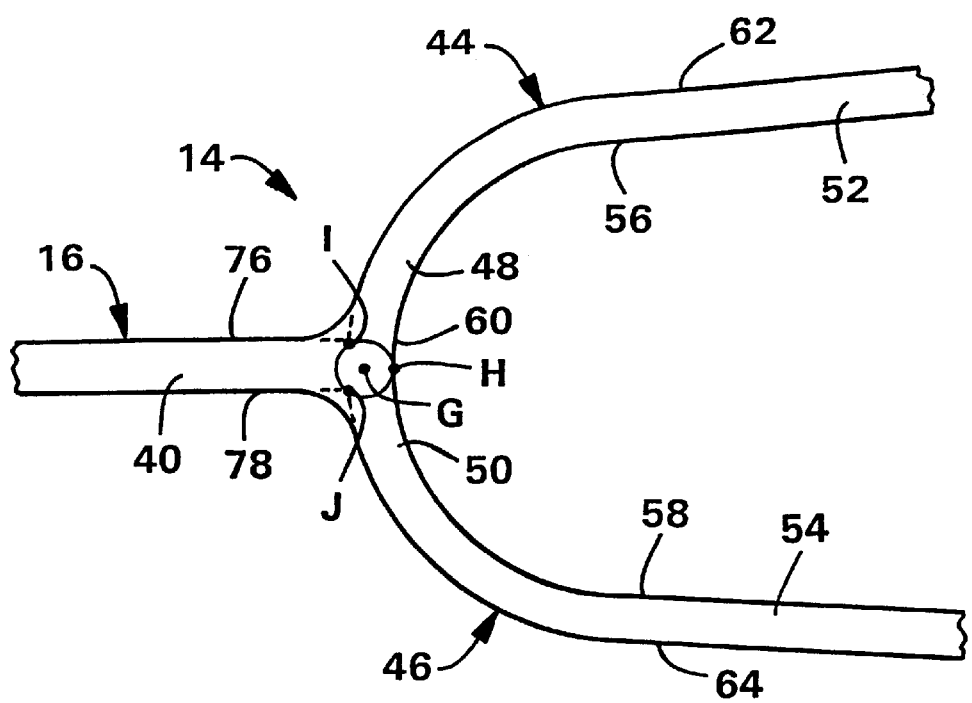
FIG. 6 is an exploded top view of the knife profile located within the area of the dotted circle shown in FIG. 5.

Referring now to FIG. 6, one can see that each of the second and third cutting members, 44 and 46, respectively, contains a linear section 52 and 54, respectively, which is integrally joined to the arcuate sections, 48 and 50, respectively. Furthermore, each of the second and third cutting members, 44 and 46, respectively, has an interior edge, 56 and 58, respectively. Both of the interior edges 56 and 58 can join one another to form a circular arc 60 between the second and third cutting members, 44 and 46, respectively. The circular arc 60 can be formed on any given radius and can be in the shape of a semi-circular arc of about 180° or be in the shape of an arc of less than 180°. When the first, second, and third cutting members, 40, 44, and 46, respectively, are machined from a single piece of metal, it is advantageous to form the arc 60 with an arc of about 180°.

Figure 7:
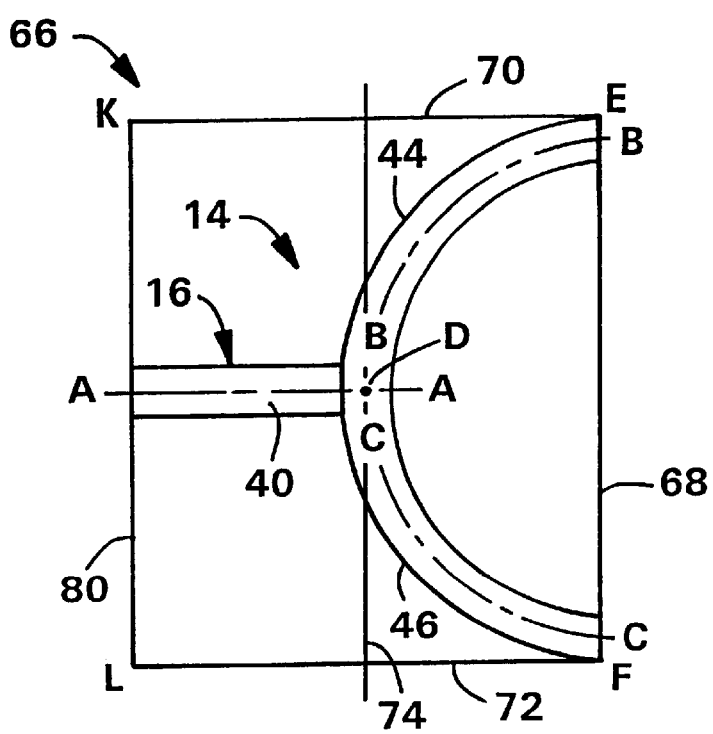
FIG. 7 is a portion of the view shown in FIG. 6 depicting a rectangle drawn about the bifurcation point of the knife.

Referring to both FIGS. 6 and 7, the second and third cutting members, 44 and 46, respectively, also contain an outside edge, 62 and 64, respectively. Each of the first, second, and third cutting members 40, 44, and 46, respectively, also contain a centerline A—A, B—B, and C—C, respectively, as shown in FIG. 7. The centerline for the first cutting member 40 will be a linear line while the centerline for the arcuate shaped portions of the second and third cutting members, 44 and 46, respectively, will be curved or arcuate shaped. The center lines B—B and C—C of the second and third cutting members, 44 and 46, respectively, will join at a point "D" which is equal distance between two vertically aligned points located the outside edges 62 and 64 of the second and third cutting members, 44 and 46, respectively.

The unique configuration of the knife 14 can be described as a ratio of the area of the cutting surface of the knife 14 to the total surface area of a rectangle formed about the intersection of at least two of the first, second and third cutting members 40, 44, and 46, respectively. The rectangle can be drawn about the point of intersection "D" using the following procedure. A rectangle 66 is formed by drawing a first line 68 through two points. Each of the points being located on one of the outside edges 62 and 64 of the second and third cutting members, 44 and 46, respectively, at a location where the respective arcuate section 48 and 50 are joined to the respective linear sections 52 and 54. By doing so, a point "E" is established on the outside edge 62 of the second cutting member 44, and a point "F" is established on the outside edge 64 of the third cutting member 46. It should be noted that point "D" is at an equal distance between points "E and F." A second line 70 and a third line 72 then are drawn perpendicular to the first line 68 at locations where the first line 68 crosses the outside edges 62 and 64 of the second and third cutting members, 44 and 46, respectively. The lines 70 and 72 perpendicularly intersect the first line 68 at points "E" and "F," respectively. A fourth line 74 then is drawn parallel to the first line 68 such that it passes through a point "G" as shown in FIG. 6. Point "G" represents the center of the smallest diameter circle which can be inscribed at the intersection of the first cutting members 40 with at least one of the second and third cutting members 44 and 46, respectively, while tangentially touching points "H," "I," and "J."

Point "H" represents a point on at least one of the arcuate sections 48 and 50 of the second and third cutting members, 44 and 46, respectively. Point "H" is located on at least one of the interior edges 56 and 58 which forms the circular arc 60. Point "I" represents the intersection or meeting point of the outer edge 76 of the first cutting member 40 with either the outside edge 62 of the second cutting member 44. If these two edges, 76 and 62, do not form a straight line, then each is extended so that they will intersect as is depicted in FIG. 6. Point "J" represents the intersection or meeting point of the outer edge 78 of the first cutting member 40 with the outside edge 64 of the third cutting member 46. If these two edges, 78 and 64, do not form a straight line, then each is extended so that they will intersect as is depicted in FIG. 6. The circumference of the circle then will contact points "H," "I," and "J" tangentially, and the center of the circle will be point "G." When only point "J" is known, a circle is drawn so that its outer circumference touch point "J" as well as tangentially touching the outside edge 62 or 64 and the interior edge 56 or 58.

Figure 8:
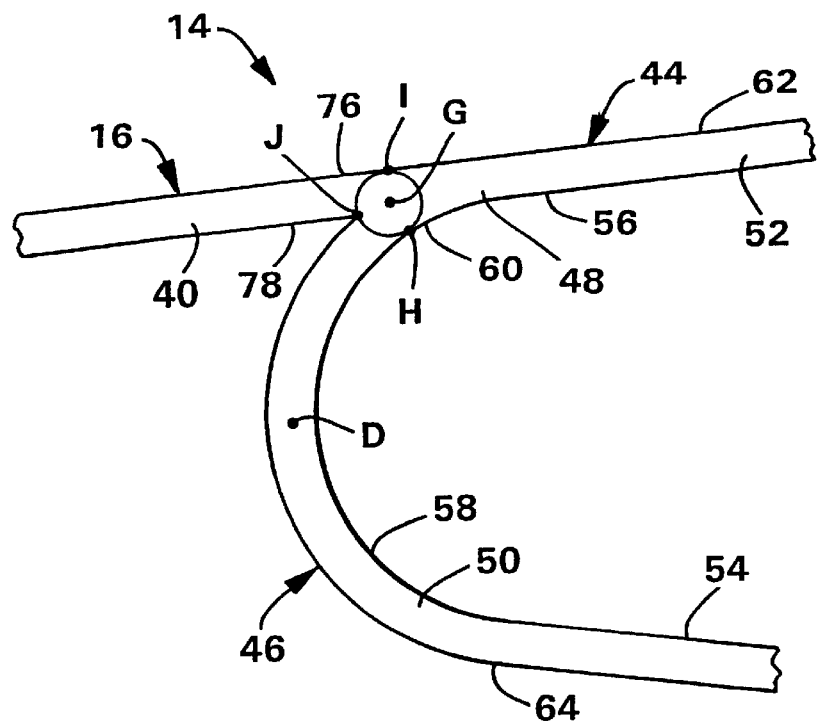
FIG. 8 is an exploded view of an alternative knife profile located within the area of the dotted circle shown in FIG. 5.

Whether the outer circumference of the circle actually contacts the outer edges 76 and 78 of the first cutting member 40 or an extension of the outer edges 76 and 78 will depend on the angle and location at which the first cutting member 40 intersects the second and/or third cutting members, 44 and 46, respectively. For example, in FIG. 6, the first cutting member 40 intersects the second and third cutting members, 44 and 46, respectively, at a location wherein the second cutting member 44 is identical in length to the third cutting member 46. In this configuration, it is necessary to extend the outer edges 76 and 78 such that they intersect the outside edges 62 and 64 at locations whereby the circle having a center point "G" can be circumscribed. In contrast, the configuration shown in FIG. 8 depicts the first cutting member 40 being offset relative to the second and third cutting members, 44 and 46. In this configuration, point "I" is located at the point where the outer edge 76 meets the outside edge 62 and point "J" is located at a point where the outer edge 78 intersects with the outside edge 64. The establishment of the circle now should be understood relative to the different configurations which are possible for the knife 14.

Referring again to FIG. 7, it should be noted that when the first cutting member 40 equally bisects the second and third cutting members, 44 and 46, respectively, it forms a "mirror image" along the longitudinal center line A—A. By a "mirror image," it is meant that the upper half of the knife 14 is a reflection of the lower half of the knife 14. The entire image of the knife 14 is very much like a tuning fork which can be used to tune musical instruments. In FIG. 7, the centerline A—A of the first cutting member 40 intersects point "D," the point where the center lines B—B and C—C of the second and third cutting members, 44 and 46, respectively, meet.

Returning to the formation of the rectangle 66, the fourth line 74 will be drawn parallel to the first line 68 and will pass through the point "G." A fifth line 80 then is drawn parallel to the fourth line 74 and at a distance from the fourth line 74 equal to the distance between the first and fourth lines, 68 and 74, respectively. It should be noted that when forming the rectangle 66, both the fourth line 74 and the fifth line 80 will be located to the same side of the first line 68. The fifth line 80 will be drawn such that it intersects the second and third lines, 70 and 72, respectively, to form points "K" and "L." The rectangle 66 then will encompass an area bounded by the points "E," "F," "L," and "K." This bounded area is referred to, for purposes of this detailed description of the present invention, as the total surface area of the rectangle 66.

For clarity, the rectangle may be referred to as a rectangle drawn over the wishbone configuration and formed by a first rectangle line between each of two rectangle corner points located on the outside edges of the second and the third cutting members, respectively, at a location where the respective arcuate section is joined to the linear section, a second rectangle side line and a third rectangle side line perpendicular to the first rectangle side line at each of the two rectangle corner points and extending a distance through a centerline positioned where the second cutting member joins the third cutting member, and a fourth rectangle side line parallel to the first rectangle side line at a distance from the center line equal to the distance between the first rectangle side line and the c enter line, the fourth rectangle side line intersecting the second and third rectangle side lines to form the rectangle within the first, second, third, and fourth rectangle side lines.

It is important that the rectangle 66 be constructed according to the above method so that the total surface area for the rectangle 66 can be established. When this is accomplished, the area of the cutting surface of any knife configuration can be compared to the total surface area of the rectangle 66. The total surface area of any two rectangles, formed by the above method, do not have to be equal but should be close in dimensions. For different knife configurations and different knife thicknesses, the total surface area for the rectangles 66 can be different when measured to the third or fourth decimal place.

The total surface area of the rectangle 66 can be calculated by multiplying its length times its width. One then will measure the area of the cutting surface of the knife 14 which is present within the total surface area of the rectangle 66 using mathematical principles and formulas. It should be noted that the area of the cutting surface area of the knife 14 can be calculated using a Cad-Cam program. Cad-Cam programs are available commercially.

Referring to Table 1 below, several calculations have been performed by varying the thickness of the first, second, and third cutting members, 40, 44, and 46, respectively. For each calculation, all three cutting members 40, 44, and 46 have approximately the same thickness, that being either 0.001 inches (0.025 mm), 0.002 inches (0.050 mm), or 0.005 inches (0.127 mm). For cutting absorbent articles, e.g., such as sanitary napkins and panty liners, it is not recommended to use a knife thickness of greater than about 0.005 inches (about 0.127 mm). The total surface area of the rectangle 66 and the area of the cutting surface of the knife 14, in $in^2$ and $mm^2$ also has been calculated. One will see that the area of the cutting surface of the knife 14 as a percent of the total surface area of the rectangular 66 will vary depending upon the thickness of the cutting members 40, 44, and 46, as well as the angle and the location of the intersection of the first cutting member 40 relative to the second and third cutting members, 44 and 46, respectively. It also should be realized that the thicknesses of the three cutting members 40, 44, and 46 do not have to be the same.

TABLE 1

| Thickness in inches (mm) | Total Surface Area of Rectangle $(in^2)$ $(mm^2)$ | Area of the Cutting Surface of the Knife $(in^2)$ $(mm^2)$ | Area of the Knife as % of rectangle |
| --- | --- | --- | --- |
| .001 (.025) | .00012 (.07742) | .000025 (.016130) | 20.83 |
| .001 (.025) | .00012 (.07742) | .00002 (.01290) | 30.77 |
| .002 (.050) | .00013 (.08387) | .00004 (.02580) | 30.77 |
| .002 (.050) | .00013 (.08387) | .00005 (.03226) | 38.46 |
| .005 (.127) | .00016 (.10323) | .0001 (.0645) | 62.50 |
| .005 (.127) | .00016 (.10323) | .0001 (.0645) | 68.75 |

NOTE:
1 in = 25.4 mm.
1 $in^2$ = 64.52 $mm^2$

Referring again to FIG. 7, the area of the cutting surface of the knife 14 represents 30.77% of the total surface area of the rectangle 66. The 30.77% was obtained when each of the first, second, and third cutting members, 40, 44, and 46, respectively, had a thickness of approximately 0.001 inches (approximately 0.025 mm). As the thickness of the knife 14 gets larger and as the angle changes at which the first member 40 intersects the second and third cutting members, 44 and 46, respectively, the area of the cutting surface of the knife 14 within the total surface area of the rectangle 66 will change.

Figure 9:
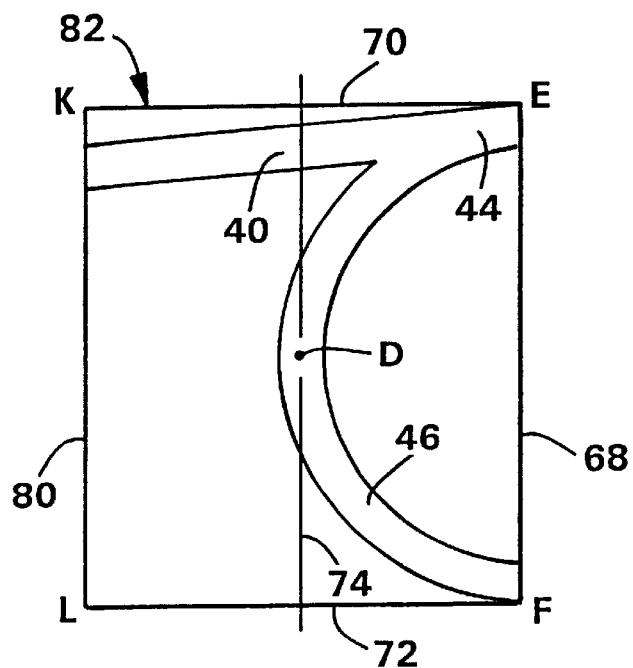
FIG. 9 is a portion of the view shown in FIG. 8 depicting a rectangle drawn about the bifurcation point of the knife.

Referring to FIGS. 8 and 9, the first, second, and third cutting members, 40, 44, and 46, respectively, also have a thickness of 0.001 inches (0.025 mm), but the first cutting member 40 intersects the second member 44 at an offset angle. The formation of the rectangle 82 is identical to that described above for rectangle 66, shown in FIG. 7. In fact, the rectangle 82 has corner points "E," "F," "L," and "K" and lines 68, 70, 72, and 80. For the knife profile shown in FIG. 9, the area of the cutting surface of the knife 14 is 20.83% of the total surface area of a rectangle 82. The reason that the area of the cutting surface of the knife 14 is less in FIG. 9, than in FIG. 7, is that the first cutting member 40 is offset from the second cutting member 44. This forms a non-symmetrical arrangement between the second and third cutting members, 44, and 46, respectively. In this arrangement, less surface area of the second cutting member 44 is included in the calculation and hence a lower ratio is obtained.

Similar calculations were made for the knife 14 when the thickness of the first, second, and third cutting members, 40, 44, and 46, respectively, increased to 0.002 inches (0.050 mm). In this case, the area of the cutting surface of the knife represented 30.77% of the total surface area of the rectangle when the knife 14 was similar in appearance to that shown in FIG. 6 and 38.46% of the total surface area of the rectangle when the knife 14 was similar in appearance to that shown in FIG. 8.

Figure 10:
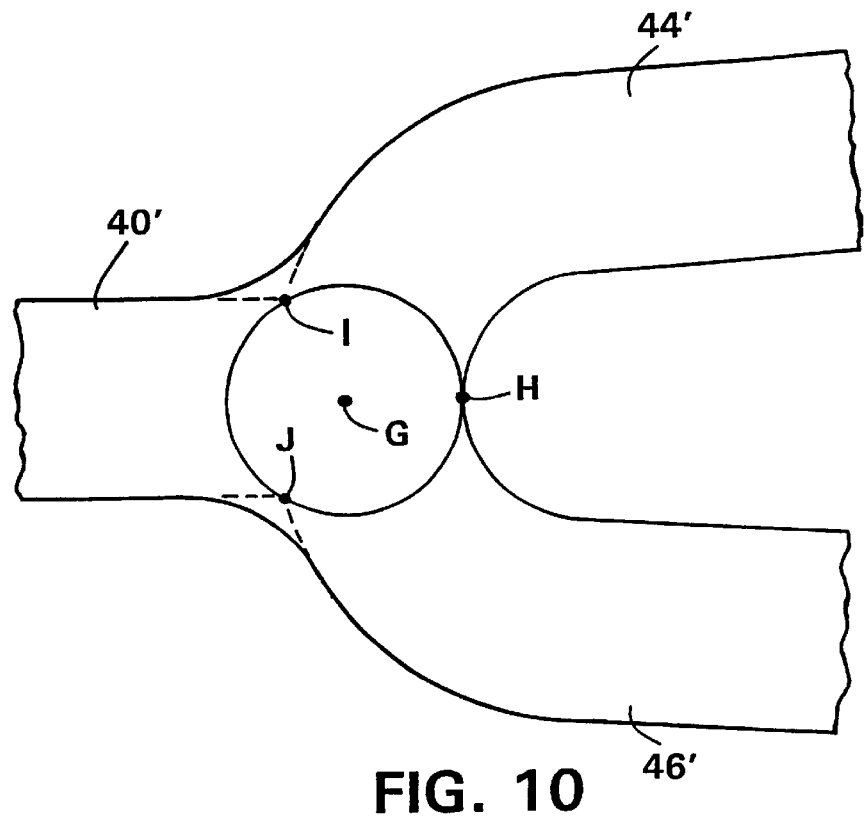
FIG. 10 is an exploded view of an alternative knife profile located within the area of the dotted circle shown in FIG. 5.
Figure 11:
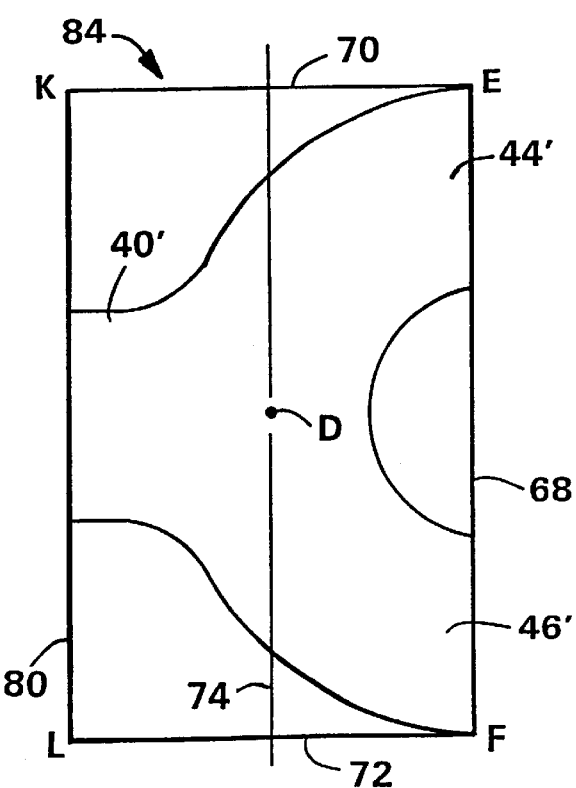
FIG. 11 is a portion of the view shown in FIG. 10 depicting a rectangle drawn about the bifurcation point of the knife.

Referring now to FIGS. 10 and 11, similar calculations were made by varying the thickness of the first, second, and third cutting members, 40', 44', and 46', respectively, such that they all had a thickness of 0.005 inches (0.127 mm). In FIG. 11, the area of the cutting surface of the knife 14 was calculated to be 62.5% of the total surface area of the rectangle 84.

Figure 12:
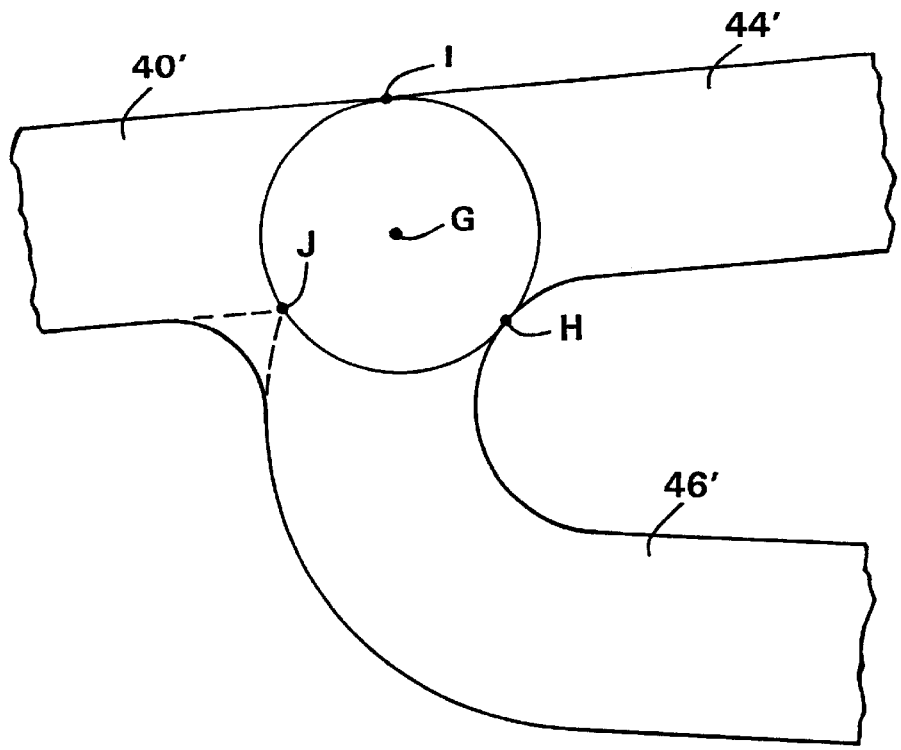
FIG. 12 is an exploded view of still another alternative knife profile located within the area of the dotted circle shown in FIG. 5.
Figure 13:
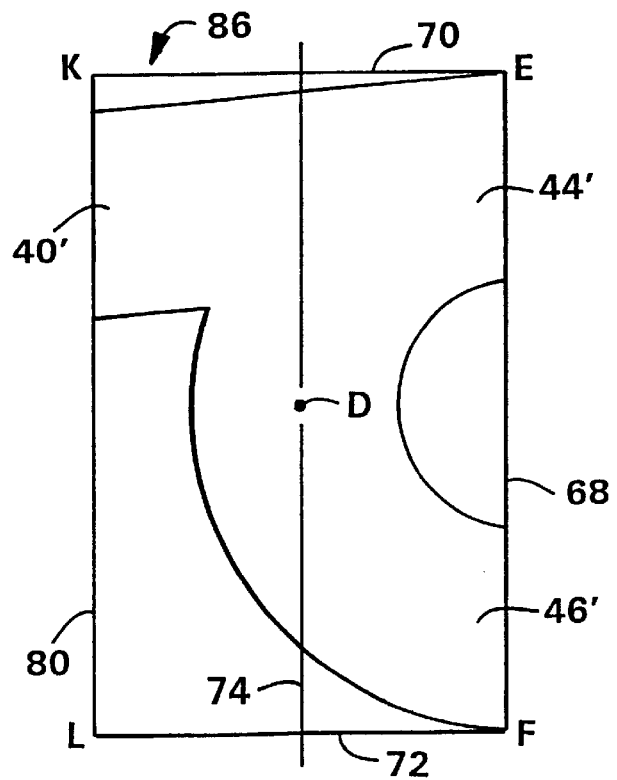
FIG. 13 a portion of the view shown in FIG. 12 depicting a rectangle drawn about the bifurcation point of the knife.

Referring to FIGS. 12 and 13, calculations were made for the three cutting members, 40', 44', and 46', respectively, when they each had a thickness of 0.005 inches (0.127 mm), and the first cutting member 40' was offset relative to the second cutting member 44'. The area of the cutting surface of the knife 14 was calculated to be 68.75% of the total surface area of the rectangle 86. The above calculations are all listed in Table 1 above.

The non-symmetrical heavy duty knife and cutting method of the present invention employs a cutting edge knife thickness in the range of about 0.003 inches to about 0.005 inches.

It should be noted that the area of the cutting surface of the knife 14 can represent from between about up about 70% of the total surface area of the rectangle. More particularly, the area of the cutting surface of the knife 14 can represent from between about 20% to about 70% of the total surface area of the rectangle.

It has been found that such a knife 14 is extremely useful in cutting absorbent products because the common edge 16 decreases the amount of trim waste which would normally be present between two adjacent but non-abutting knives. By reducing the amount of trim waste, one can obtain a more efficient operation using less raw material. The common edge 16 of the knife 14 is able to cut a portion of the outer periphery of two adjacent products with a single cut and therefore can increase production of multiple products.

While the invention has been described in conjunction with several specific embodiments, it is to be understood that many alternatives, modifications, and variations will be apparent in light of the foregoing description. Accordingly, this invention is intended to embrace all such alternatives, modifications, and variations which fall within the spirit and scope of the appended claims.

What is claimed is:

1. A knife, comprising:
    a) a linear first cutting member having a first end;
    b) a linear second cutting member joined to said first end of said first cutting member;
    c) a third cutting member having a linear section and an arcuate section joined to said first end of said first cutting member and further joined to said linear second cutting member;
    d) a non-symmetrical configuration formed by said linear second cutting member joined to said first end of said first cutting member cooperating with said third cutting member having a linear section and an arcuate section joined to said first end of said first cutting member and further joined to said linear second cutting member;
    e) a cutting edge on said first, said second, and said third cutting members having a cutting edge knife thickness in the range of greater than 0.003 inches to about 0.005 inches; and
    f) a cutting edge surface area in the range of up to about 70% of the total surface area of a rectangle drawn over said non-symmetrical configuration and formed by a first rectangle side line between each of two rectangle corner points located on said outside edges of said second and said third cutting members, respectively, at a location where said respective arcuate section is joined to said linear section, a second rectangle side line and a third rectangle side line perpendicular to said first rectangle side line at each of said two rectangle corner points and extending a distance through a centerline positioned where said second cutting member joins said third cutting member, and a fourth rectangle side line parallel to said first rectangle side line at a distance from said center line equal to the distance between said first rectangle side line and said center line, said fourth rectangle side line intersecting said second and third rectangle side lines to form said rectangle within said first, second, third, and fourth rectangle side lines.

2. A knife as set forth in claim 1, wherein said knife is machined from the outer periphery of a rotary shaft and integrally formed into said shaft.

3. A knife as set forth in claim 2, wherein said cutting edge has a cutting depth in the range of about 1/8 inch to about 3/16 inch.

4. A knife as set forth in claim 3, wherein said first cutting member intersects said second cutting member cutting edge at an offset angle.

5. A knife as set forth in claim 4, wherein said knife is composed of tool steel.

6. A method of cutting a sanitary napkin from a layered absorbent material web, comprising:
    a) providing a linear first cutting member having a first end;
    b) providing a linear second cutting member joined to said first end of said first cutting member;
    c) providing a third cutting member having a linear section and an arcuate section joined to said first end of said first cutting member and further joined to said linear second cutting member;
    d) providing a non-symmetrical configuration formed by said linear second cutting member and said third cutting member cooperating with said first cutting member and having an outside edge and an arcuately shaped centerline;
    e) providing a cutting edge on said first, said second, and said third cutting members having a cutting edge knife thickness in the range of greater than 0.003 inches to about 0.005 inches; and
    f) providing a cutting edge surface area in the range of up to about 70 of the total surface area of a rectangle drawn over said non-symmetrical configuration and formed by a first rectangle line between each of two rectangle corner points located on said outside edges of said second and said third cutting members, respectively, at a location where said respective arcuate section is joined to said linear section, a second rectangle side line and a third rectangle side line perpendicular to said first rectangle side line at each of said two rectangle corner points and extending a distance through a centerline positioned where said second cutting member joins said third cutting member, and a fourth rectangle side line parallel to said first rectangle side line at a distance from said center line equal to the distance between said first rectangle side line and said center line, said fourth rectangle side line intersecting said second and third rectangle side lines to form said rectangle within said first, second, third, and fourth rectangle side lines.

7. A method of cutting a sanitary napkin from a layered absorbent material web as set forth in claim 6, wherein said cutting edge is machined from the outer periphery of a rotary shaft and integrally formed into said shaft.

8. A method of cutting a sanitary napkin from a layered absorbent material web as set forth in claim 7, wherein said cutting edge has a cutting depth in the range of about 1/8 inch to about 3/16 inch.

9. A method of cutting a sanitary napkin from a layered absorbent material web as set forth in claim 8, further comprising positioning said cutting edge at a proximity from a corresponding anvil to cut through only about 80% to 90% of the thickness of said layered absorbent material web.

10. A method of cutting a sanitary napkin from a layered absorbent material web as set forth in claim 9, wherein said first cutting member intersects said second cutting member cutting edge at an offset angle.

11. A method of cutting a sanitary napkin from a layered absorbent material web as set forth in claim 10, wherein said cutting edge is composed of tool steel.

12. A method of cutting a sanitary napkin from a layered absorbent material web as set forth in claim 11, wherein said layered absorbent material web is less than about 3/32 inch thick.

13. A method of cutting a sanitary napkin from a layered absorbent material web as set forth in claim 11, wherein said sanitary pad comprises a panty liner.

14. A knife, comprising:
 a) a first cutting member having a first end;
 b) a second cutting member joined to said first end of said first cutting member, said second cutting member having an interior edge; and
 c) a third cutting member joined to said first end of said first cutting member, said third cutting member having an interior edge joining said second cutting member having an interior edge to form a circular arc between said second and third cutting members, said second and said third cutting members being arranged relative to one another to form an angle there between of from between about 30° to about 150°, said second cutting member having a linear section and said third cutting member having an arcuate section which cooperate with said first cutting member to form a non-symmetrical configuration, said third cutting member having a linear section integrally joined to said arcuate section and said first, said second, and said third cutting members having a same knife thickness, said knife thickness ranging from between greater than 0.003 inches to about 0.005 inches; and
 d) wherein each of said second and third cutting members has an outside edge and when a rectangle is drawn about the point of intersection of said first, second and third cutting members, the area of cutting surface of said knife is up to about 70% of the total surface area of said rectangle, said rectangle being formed by drawing a first line through two points, each of said points being located on one of said outside edges of said second and third cutting members, respectively, at a location where said arcuate section is joined to said linear section, a second line and a third line are then drawn perpendicularly to said first line at locations where said first line crosses said outside edges of said second and third cutting members, respectively, a fourth line is then drawn parallel to said first line such that it passes through a point where the centerline of said second cutting member joins the centerline of said third cutting member, and a fifth line is drawn parallel to said fourth line and at a distance from said fourth line which is equal to the distance between said first and fourth lines, said fifth line being drawn on the same side of the first line as is the fourth line, and said fifth line said second and third rectangle side lines to form said rectangle within said first, second, third, and fourth rectangle side lines.

15. The knife of claim 14, wherein said first cutting member is linear.

16. The knife of claim 14, wherein said first cutting member is non-linear.

17. The knife of claim 1, wherein said first cutting member, said second cutting member, and said third cutting member have a thickness of about 0.005 inch.

* * * * *

UNITED STATES PATENT AND TRADEMARK OFFICE
CERTIFICATE OF CORRECTION

PATENT NO.     : 6,305,260 B1
DATED          : October 23, 2001
INVENTOR(S)    : Peter Truttmann, Jeffrey Allen Plamann, John Glen Ahles, Robert Lee Holewinski, Brian Dennis Clare and Timothy Noel Tease It is certified that error appears in the above-identified patent and that said Letters Patent is hereby corrected as shown below:

<u>Column 14,</u>
Line 43, insert -- % -- after "70"

Signed and Sealed this

Third Day of December, 2002

JAMES E. ROGAN
*Director of the United States Patent and Trademark Office*